(12) United States Patent
Engelhardt et al.

(10) Patent No.: US 6,614,031 B2
(45) Date of Patent: Sep. 2, 2003

(54) METHOD FOR EXAMINING A SPECIMEN, AND CONFOCAL SCANNING MICROSCOPE

(75) Inventors: Johann Engelhardt, Bad Schoenborn (DE); Juergen Hoffmann, Wiesbaden (DE); Werner Knebel, Kronau (DE)

(73) Assignee: Leica Microsystems Heidelberg GmbH, Mannheim (DE)

( * ) Notice: Subject to any disclaimer, the term of this patent is extended or adjusted under 35 U.S.C. 154(b) by 162 days.

(21) Appl. No.: 09/946,695

(22) Filed: Sep. 4, 2001

(65) Prior Publication Data

US 2002/0027203 A1 Mar. 7, 2002

(30) Foreign Application Priority Data

Sep. 5, 2000 (DE) .......................................... 100 43 986

(51) Int. Cl.⁷ ........................ H01N 21/268; G01N 21/64
(52) U.S. Cl. ................... 250/459.1; 250/458.1
(58) Field of Search .......................... 250/459.1, 458.1, 250/461.1, 461.2, 484.4, 487.1

(56) References Cited

U.S. PATENT DOCUMENTS

| | | | | |
|---|---|---|---|---|
| 5,091,652 A | * | 2/1992 | Mathies et al. | 250/458.1 |
| 5,117,466 A | * | 5/1992 | Buican et al. | 382/133 |
| 6,259,104 B1 | * | 7/2001 | Baer | 250/492.2 |
| 6,300,639 B1 | * | 10/2001 | Wiederhoeft | 250/458.1 |

FOREIGN PATENT DOCUMENTS

DE          19829981          1/2000

OTHER PUBLICATIONS

LeicaTCS 4D UV—"The System Concept for Multiparameter Confocal Microscopy", Scientific and Technical Information vol. XI,No. 1,pp 9–19, Jun. 1995.

P.Wedekind et al., "Scanning microphotolysis: a new photobleaching technique based on fast intensity modulation of a scanned laser beam and confocal imaging", Journal of Microscopy, vol 176, Part 1, Oct. 1994, pp 23–33.

* cited by examiner

Primary Examiner—Constantine Hannaher
Assistant Examiner—Otilia Gabor
(74) Attorney, Agent, or Firm—Davidson, Davidson & Kappel, LLC

(57) ABSTRACT

A method for examining a specimen (11) by means of a confocal scanning microscope having at least one light source (1), preferably a laser, to generate an illuminating light beam (4) for the specimen (11), and a beam deflection device (9) to guide the illuminating light beam (4) over the specimen (11) comprises, in the interest of reliable definition of details or regions of interest of the specimen (11), the following method steps: Firstly a preview image is acquired. Then at least one region of interest in the preview image is marked. This is followed by allocation of individual illuminating light beam wavelengths and/or illuminating light beam power levels to the region or regions. Illumination of the region or regions of the specimen (11) in accordance with the allocation is then accomplished, at least one manipulation in at least one region (25) being performed by means of the illumination. Also described is a confocal scanning microscope having at least one light source (1), preferably a laser, to generate an illuminating light beam (4) for a specimen (11), and a beam deflection device (9) to guide the illuminating light beam (4) over the specimen (11), means for acquiring a preview image and means for marking at least one region of interest in the preview image being provided, such that individual illuminating light beam wavelengths and/or illuminating light beam power levels can be allocated to the region or regions, and the region or regions of the specimen (11) can be illuminated in accordance with the allocation, and such that at least one manipulation in at least one region (25) can be performed by means of the illumination.

33 Claims, 6 Drawing Sheets

METHOD FOR EXAMINING A SPECIMEN, AND CONFOCAL SCANNING MICROSCOPE

FIELD OF THE INVENTION

The present invention concerns a method for examining a specimen by means of a confocal scanning microscope having at least one light source, preferably a laser, to generate an illuminating light beam for the specimen, and a beam deflection device to guide the illuminating light beam over the specimen.

The present invention further concerns a confocal scanning microscope having at least one light source, preferably a laser, to generate an illuminating light beam for a specimen, and a beam deflection device to guide the illuminating light beam over the specimen.

BACKGROUND OF THE INVENTION

A method for examining a specimen by means of a scanning microscope, and a confocal scanning microscope, of the kinds cited above are known from practical use. In known scanning microscopy, a specimen is illuminated with an illuminating light beam for the specimen in order to observe the reflected or fluorescent light emitted from the specimen. The focus of the illuminating light beam is generally moved in one specimen plane by tilting two mirrors, the deflection axes usually being perpendicular to one another so that one mirror deflects in the X direction and the other in the Y direction. The tilting of the mirrors that substantially constitute the beam deflection device is brought about, for example, with the aid of galvanometer positioning elements, both fast resonant galvanometers as well as slower and more accurate non-resonant galvanometers being used. The power of the light coming from the specimen is measured as a function of the position of the scanning beam or illuminating light beam.

In confocal scanning microscopy specifically, a specimen is scanned in three dimensions with the focus of an illuminating light beam. A confocal scanning microscope generally comprises a light source, a focusing optical system with which the light of the light source is focused onto a pinhole, a beam splitter, a beam deflection device for beam control, a microscope optical system, a detection pinhole, and detectors for detecting the detected or fluorescent light. The illuminating light or illuminating light beam must usually be coupled in via a beam splitter. The fluorescent or reflected light coming from the specimen passes, in the most commonly used descan arrangement, via the same scanning mirrors or the same beam deflection device back to the beam splitter and passes through the latter, then being focused onto the detection pinhole behind which the detectors (usually photomultipliers) are located. Detected light that does not derive directly from the focus region takes a different light path and does not pass through the detection stop; what is obtained is a point datum that results, by way of sequential scanning of the specimen, in a three-dimensional image. A three-dimensional image is usually achieved by acquiring image data in layers.

At present, specimens are usually illuminated over the entire scan field with light of one wavelength, or simultaneously with light of several wavelengths. For this reason, comparative examinations whose purpose is to examine specimens under different spectral illumination conditions but under otherwise identical boundary conditions are performed sequentially on one specimen or sequentially on identically prepared specimens.

In cell biology, specimens are often prepared with compounds that contain calcium or amino acids such as glutamate. These "caged" compounds comprise on the one hand the caged calcium or glutamate, and on the other hand the so-called complexing agents or gelators. These compounds can be broken up by irradiation with UV light or by two-photon processes; this is referred to as "photoactivation." The calcium or glutamate that is released is then capable of initiating further reactions.

Ideally, the track of the deflected illuminating light beam on the specimen surface —or, in the case of a confocal arrangement, in a layer plane in the specimen—should describe a meander. This involves first scanning a line in the X direction at a constant Y position, then a Y displacement with no change in X position, and then scanning a line in the negative X position at a constant Y position. In reality, because of the inertia of the moving galvanometer components and the mirrors of the beam deflection device, a meander shape of this kind can be approximately achieved only for low scanning rates. At reasonable scanning rates of more than 100 Hz, the scanning track of the illuminating light beam actually describes a sine-like curve, which creates the need for correction of the resulting deviations from the ideal situation. For example, the track speed in the vicinity of the reversal points is lower than in the linear sine region, resulting (inter alia) in greater bleaching in those regions. It has therefore been usual for some time to interrupt the specimen illumination while passing through the reversing portions, using mechanical stops that limit the image field or by means of suitable optical arrangements— for example with acoustooptical modulators (AOTFs). This technique of interrupting the beam during scanning is called "blanking." An arrangement with mechanical stops was incorporated as early as 1990 in a confocal laser scanning microscope of the applicant. An arrangement having an acoustooptical modulator is described in Scientific and Technical Information Vol. XI, No. 1, pp. 9–19, Jun. 1995, "Leica TCS 4D UV—The system concept for Multiparameter Confocal Microscopy." This document explains the sine-like trajectory and the problems associated with it, although blanking is not explicitly mentioned. Controlled bleaching-out of any desired predefinable specimen regions using an AOTF arrangement, which makes it possible to illuminate various regions of a specimen with different light intensities, is described in P. Wedekind et al., "Scanning microphotolysis: a new photobleaching technique based on fast intensity modulation of a scanned laser beam and confocal imaging," Journal of Microscopy, Vol. 176, Part 1, Oct. 1994, pp. 23–33. This document illustrates a blanking technique at a very high technical level.

The German Patent Application DE 198 29 981 of Carl Zeiss Jena GmbH, "Method and arrangement for confocal microscopy," describes the elimination of the bleaching problem, and additionally the elimination of bleed-through, by the fact that the spectral composition and/or the intensity of the laser light coupled into the microscope beam path is modified while deflection continues without interruption; as a result, at least two adjacent locations or scan points of the specimen are impinged upon by light of differing spectral properties and/or different intensity.

A problem with the known method and the known confocal scanning microscope is that it is not clear how a detail of a specimen that is to be evaluated can be selected for differentiated illumination. Reliable selection and definition of the details of interest in the specimen is therefore not possible.

SUMMARY OF THE INVENTION

It is therefore the object of the present invention to make available a method for examining a specimen, wherein the method allows in a simple manner, reliable definition of details of interest of the specimen for differentiated illumination and manipulation.

According to the present invention, the aforesaid object is achieved by a method which comprises the steps of:

generating an illuminating light beam with at least one light source, deflecting the illuminating light beam with to a beam deflection device over the specimen, aquiring a preview image;

marking of at least one region of interest in the preview image;

allocating individual illuminating light beam wavelengths or illuminating light beam power levels to the at least one region;

illuminating the at least one region of the specimen in accordance with the allocation, wherein the illuminating light beam is guided such that substantially only the at least one marked region of the specimen is illuminated, and performing at least one manipulation in at least one region by means of the illumination wherein during the manipulation in the at least one region that region is simultaneously observed.

It is a further object of the invention to provide a confocal scanning microscope which allows in a simple manner, reliable definition of details of interest of the specimen for differentiated illumination and manipulation. According to this, the object is accomplished by a confocal scanning microscope comprising:

at least one light source to generate an illuminating light beam;

a beam deflection device to guide the illuminating light beam over a specimen;

a least one detector for registering the reflected and fluorescent light proceeding from the specimen;

means for acquiring a preview image of at least a part of the specimen; and means for marking at least one region of interest in the preview image, such that individual illuminating light beam and wavelengths and illuminating light beam power levels are allocated to the at least one region and thereby performing a manipulation in the at least one region.

First a preview image is acquired. This supplies to the observer a visual depiction of the specimen being examined. Marking of at least one region of interest in the preview image is then accomplished. These two method steps make possible, in a manner according to the present invention, particularly simple selection and definition of a detail of interest of a specimen. The observer simply needs to study the preview image in order then to make a marking in the preview image.

This is then followed by an allocation of individual illuminating light beam wavelengths and/or illuminating light beam power levels to the region or regions. The region or regions of the specimen is or are then illuminated in accordance with the allocation, at least one manipulation in at least one region being performed by means of the illumination. Quite individually selected regions can thereby be subjected to a manipulation.

In an advantageous embodiment of the method, during the manipulation in at least one region, that region or those regions and/or at least one other region could be substantially simultaneously observed. This eliminates the disadvantage that between a manipulation and a sequentially occurring observation, events that are unobservable or only partly observable occur. Quasi-simultaneous and location-specific manipulation and observation are thereby made possible. In this context, it is in principle also possible to manipulate and quasi-simultaneously observe the same region.

After illumination of the region or regions of the specimen, the reflected and/or fluorescent light proceeding from the specimen could be detected. An overview image of the specimen after illumination could thereby be made available.

In an advantageous embodiment of the method, in order to avoid any undesired exposure of the specimen outside the region or regions to be examined, the illuminating light beam could be guided in such a way that substantially only the marked region or regions of the specimen are illuminated. The illuminating light beam could travel the shortest distance to the selected region or regions, or between the selected regions.

Concretely, during ongoing acquisition of an overview image of at least one region, a chemical reaction could be initiated or compounds could be broken up by controlled, preferably time-limited introduction of the illuminating light of a second light source, preferably a laser. The compounds could be caged calcium or caged glutamate compounds. The reaction of at least one other region to the breaking-up operation could be observed. The second light source could be an infrared or UV laser.

Alternatively or in addition to the triggering of a chemical reaction or the breaking up of compounds, the manipulation could comprise the excision of portions of a cell nucleus or of a complete cell nucleus. This manipulation as well could be accomplished, during ongoing acquisition of an overview image, in at least one predefinable region by controlled, preferably time-limited introduction of the illuminating light of a second light source, preferably a laser.

Portions excised in this fashion could be suctioned off with a micropipette, or transported off with a laser trap. The method suitable in this context is to be selected as required.

Concretely, the method according to the present invention allows an investigation of information transmission from cell to cell. Information transport from cell to cell takes place on the one hand by way of electrical information transfer, and on the other hand by the transmission of neurotransmitters such as, for example, calcium.

In the concrete application, a cell could be marked in the preview image. Such a cell could, for example, be prepared with a caged calcium compound.

The cell could then be illuminated at a preselected point in time with UV or infrared light. The illumination is performed, in this context, in controlled and location-specific fashion.

The aforesaid caged calcium compound could thereby be broken up, and the calcium that is released could initiate a reaction in the cell. Information transmittal could be detected by observation of an adjacent cell. For that purpose, concretely, the adjacent cell could be prepared with a calcium indicator.

It is known that the reaction of the adjacent cell can fail to occur if the stimulus information of a third cell arrives within a specific time window. In particular for the investigation of this phenomenology, it may be useful to initiate a reaction in two cells quasi-simultaneously or with a defined time offset. This, too, is made possible by the method according to the present invention. It is furthermore conceivable to alternately illuminate different scan points in the two cells.

In both a two-dimensional X-Y depiction and in a three-dimensional X-Y-Z depiction, the region or regions of interest of the specimen could be selected or marked by way of a computer and preferably a computer mouse.

The allocation of individual illuminating light beam wavelengths and/or illuminating light beam power levels to the region or regions could then also be accomplished by way of a computer of this kind.

To prevent illumination of the specimen outside the region or regions, a definable blanking could be performed. In this, the illuminating light beam is interrupted in controlled fashion during scanning, so that the unmarked regions are not illuminated at all. As a result, the region or regions is or are particularly emphasized, and the unmarked remaining region of the specimen is not unnecessarily bleached out.

To achieve higher contrast and to decrease the total data acquisition time, the region or regions could be scanned more slowly and with elevated photon statistics as compared to the remainder of the specimen.

Outside the region or regions or between the regions, the specimen could be scanned at the maximum deflection speed. A further reduction in total data acquisition time could be achieved by the fact that outside the region or regions or between the regions, beam deflection deviates from sinusoidal, sawtooth-shaped, or meander-shaped beam deflection. The regions could thereby be arrived at over a shorter distance. Ideally, beam deflection between two regions or the regions could be accomplished substantially in a direct line from one region to another region.

In an advantageous embodiment, during manipulation in at least one region, that region or those regions and/or at least one other region could be substantially simultaneously observable.

Alternatively or in addition thereto, after illumination of the region or regions of the specimen, the reflected and/or fluorescent light proceeding from the specimen could be detectable.

Concretely, the confocal scanning microscope could comprise a spectrally selective element for setting the illuminating light beam wavelength or wavelengths. The spectrally selective element could be an AOTF (acoustooptical tunable filter), an AOD (acoustooptical deflector), an EOM (electrooptical modulator), or a mechanical component. Acoustooptical tunable filters are characterized by great flexibility, and make it possible to switch over the illuminating light beam wavelengths, introduce light of one or more wavelengths, or vary the light power level, very quickly, i.e. in the range of approx. 1 µs or less.

A spectrally selective element of this kind could be controllable by way of a computer, preferably as a function of the deflection position.

The confocal scanning microscope could furthermore comprise an element for adjusting the illuminating light beam power level. An element of this kind for adjusting the illuminating light beam power level could comprise an AOTF or a mechanical component. The element for adjusting the illuminating light beam power level could also be controllable by way of a computer, preferably as a function of the deflection position.

In particularly simple fashion, the same element could be usable for adjusting the illuminating light beam wavelength or wavelengths and for adjusting the illuminating light beam power level. An AOTF is particularly suitable in this context.

To make available several different illuminating light beam wavelengths, several lasers could be provided to generate the illuminating light beam. Alternatively, one or more multiple-line lasers could also be provided to generate the illuminating light beam.

A PC, on whose monitor the image or preview image of the specimen is displayed, could be usable for displaying and marking the region or regions.

The marking of a three-dimensional region or regions could be performable in an X, Y, Z depiction or in two-dimensional sectioned depictions.

In particularly simple fashion, the beam deflection device could comprise galvanometer positioning elements. Galvanometer positioning elements of this kind could preferably be controllable by way of a computer, with which the beam deflection speeds can be adapted individually to requirements in terms of the marked region or regions.

Blue semiconductor lasers or Ar lasers are preferably used for UV illumination. Ti:sapphire lasers preferably provide illumination in the infrared region.

BRIEF DESCRIPTION OF THE DRAWINGS

There are various ways of advantageously embodying and developing the teaching of the present invention. In conjunction with the explanation of the preferred exemplary embodiment of the invention with reference to the drawings, an explanation is also given of generally preferred embodiments and developments of the teaching. In the drawings.

DETAILED DESCRIPTION OF THE INVENTION

Figure 1:
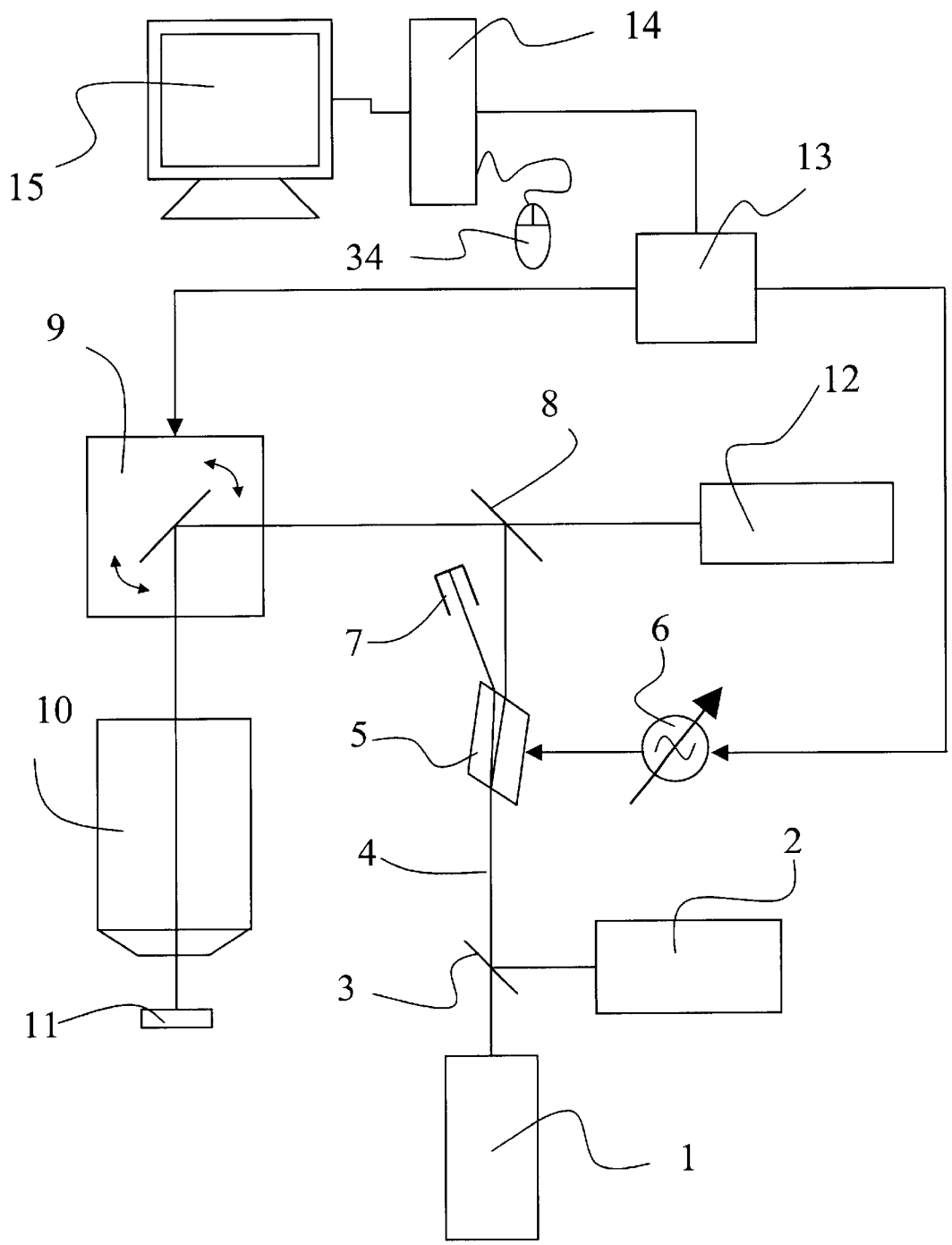
FIG. 1 schematically depicts the exemplary embodiment of a confocal scanning microscope according to the present invention.

FIG. 1 schematically depicts the exemplary embodiment of a confocal scanning microscope according to the present invention for examining a specimen 11. The confocal scanning microscope has a light source 1 in the form of a first laser. The scanning microscope furthermore has a second laser 2 in the form of a multiple-line laser. The light beams generated by the first and the second laser 2 are combined by means of a beam combiner 3 to form illuminating light beam 4.

Illuminating light beam 4 passes through an AOTF 5 that is operated by means of an AOTF high-frequency controller 6. Following AOTF 5 is a beam trap 7. The illuminating light selected by AOTF 5 is reflected by means of a main beam splitter 8 onto a beam deflection device 9. Downstream from beam deflection device 9 is an objective 10 that directs the illuminating light onto specimen 11.

Also provided is a detector 12 for fluorescent or reflected light.

A control computer 13 is provided to control AOTF high-frequency control system 6 and beam deflection device 9. Control computer 13 is coupled to a PC 14 and a monitor 15, thereby making it possible to display specimen 11 and to mark the regions of interest by means of a computer mouse 34.

Figure 2:
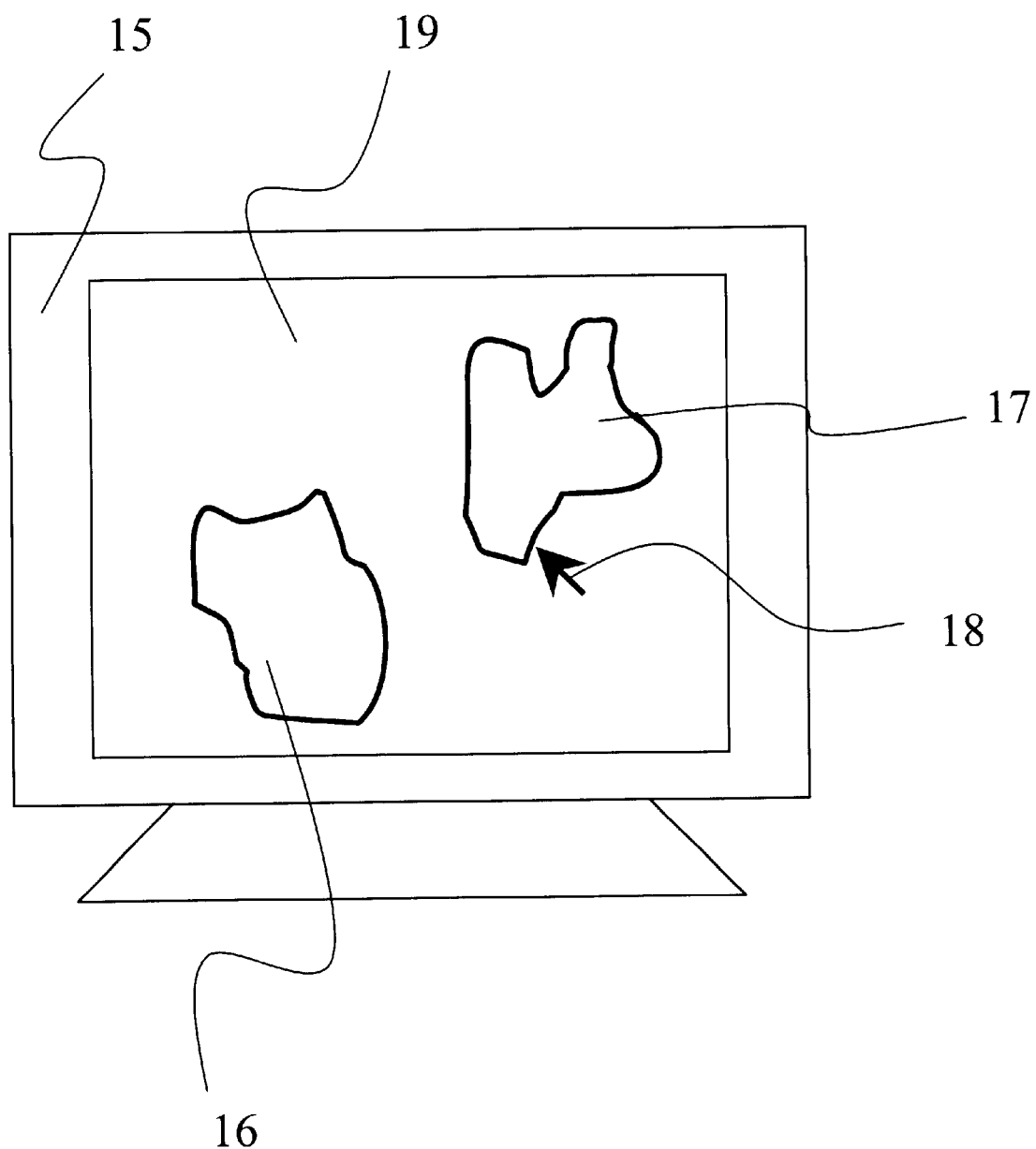
FIG. 2 schematically depicts two two-dimensional regions depicted by means of a monitor.

FIG. 2 schematically depicts two marked two-dimensional regions 16 and 17 depicted by means of monitor 15. Regions 16 and 17 are to be illuminated with light of different wavelengths. Region 16 is the region to be manipulated, in which a caged calcium compound is being broken up. In the other region 17, to be observed, the reaction to that manipulation is being observed. A cursor 18, which can be guided over preview image 19, is provided for marking regions 16 and 17. A bordering line visible to the user is drawn by pressing a mouse button while moving around regions 16 and 17.

Figure 3:
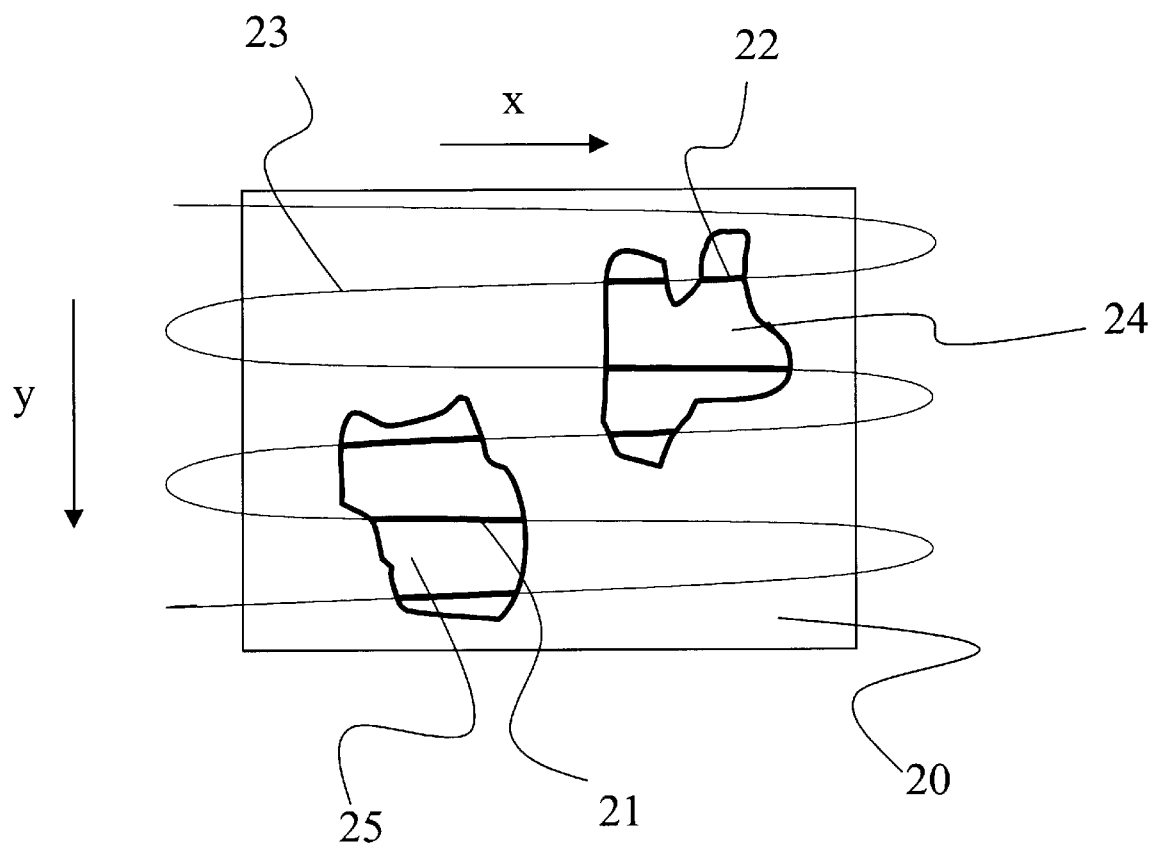
FIG. 3 schematically depicts the marked regions as shown in FIG. 2, with a sinusoidal scanning track of the illuminating light beam for the specimen.

FIG. 3 schematically depicts specimen regions 24 and 25 which correspond to marked regions 17 and 16 as shown in FIG. 2, scan field 20 being scanned sinusoidally along a scanning track 23. Specimen region 25 is subjected to an illumination 21 with wavelength $\lambda_1$, whereas specimen region 24 is subjected to an illumination 22 with wavelength $\lambda_2$.

Figure 4:
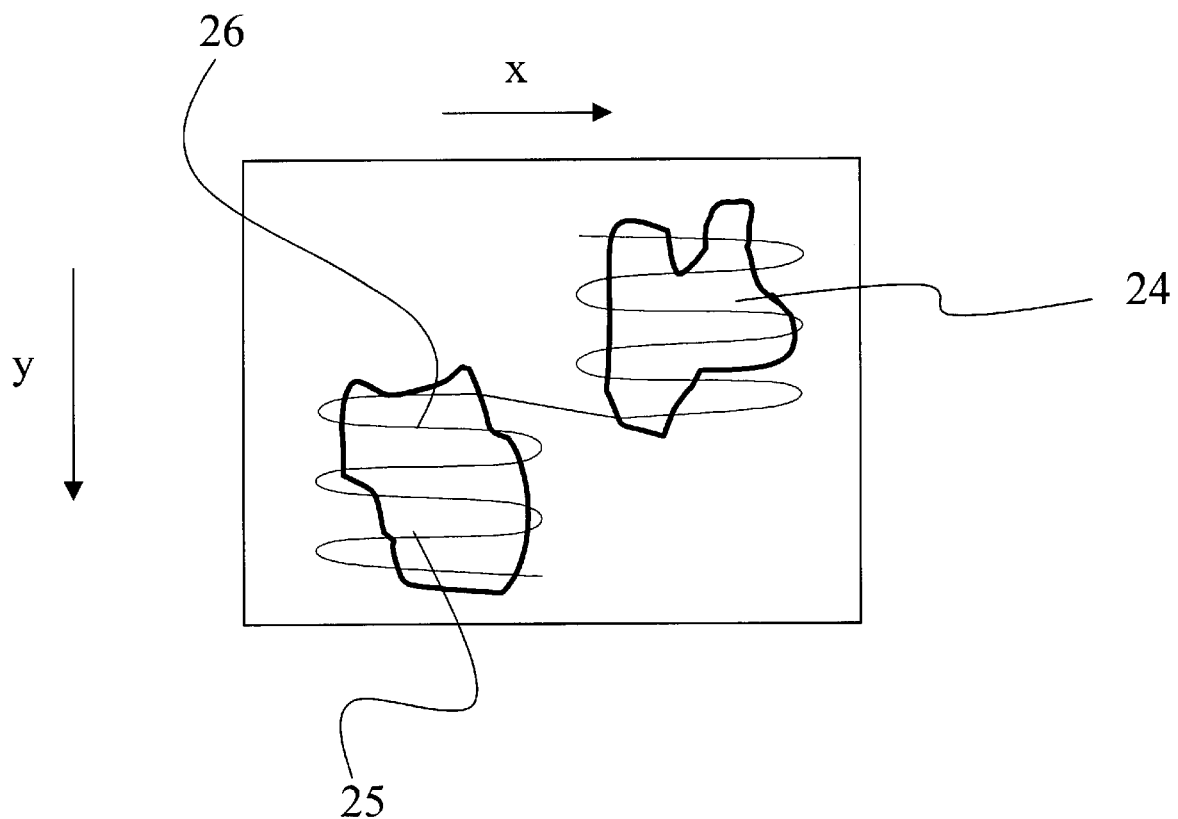
FIG. 4 schematically depicts the marked regions as shown in FIG. 2, the regions being specifically scanned.

FIG. 4 schematically depicts specimen regions 24 and 25, regions 24 and 25 being specifically scanned. For that purpose, a region-adapted scanning track 26 is generated. Beam deflection between regions 24 and 25 is accomplished substantially directly, which prevents any bleaching of specimen regions outside regions 24 and 25 and reduces the dead time between scanning of specimen regions 24 and 25. In addition, the illuminating light beam can be interrupted by means of AOTF 5 after region 24 is scanned, until the scanning of region 25 begins.

Figure 5:
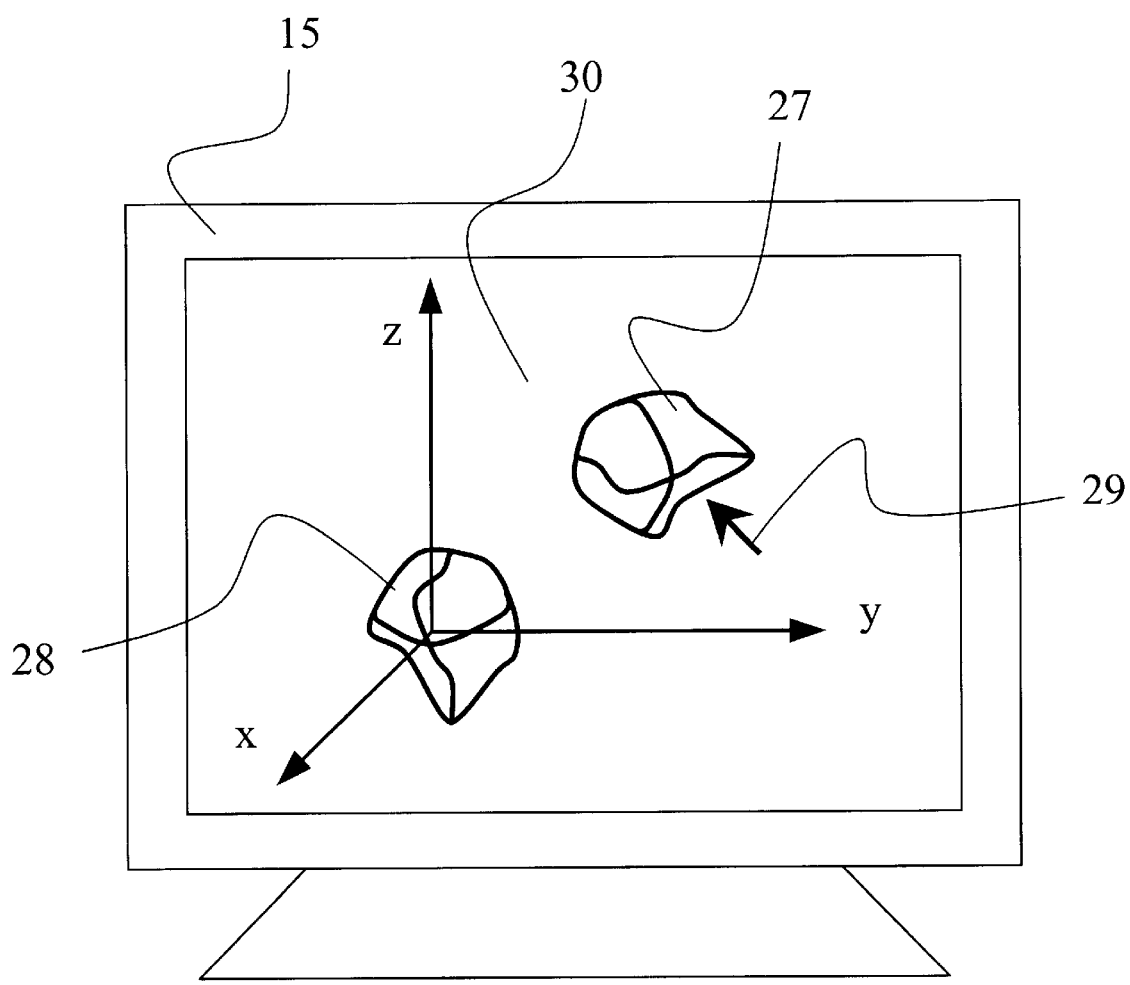
FIG. 5 schematically depicts two marked three-dimensional regions depicted by means of a monitor.

FIG. 5 schematically depicts two marked three-dimensional regions 27 and 28 depicted by means of monitor 15. Also shown is a cursor 29 for region marking. A three-dimensional preview image 30 is thereby formed. Here again, specimen regions 27 and 28 are to be illuminated with light of different wavelengths and/or different intensities.

Figure 6:
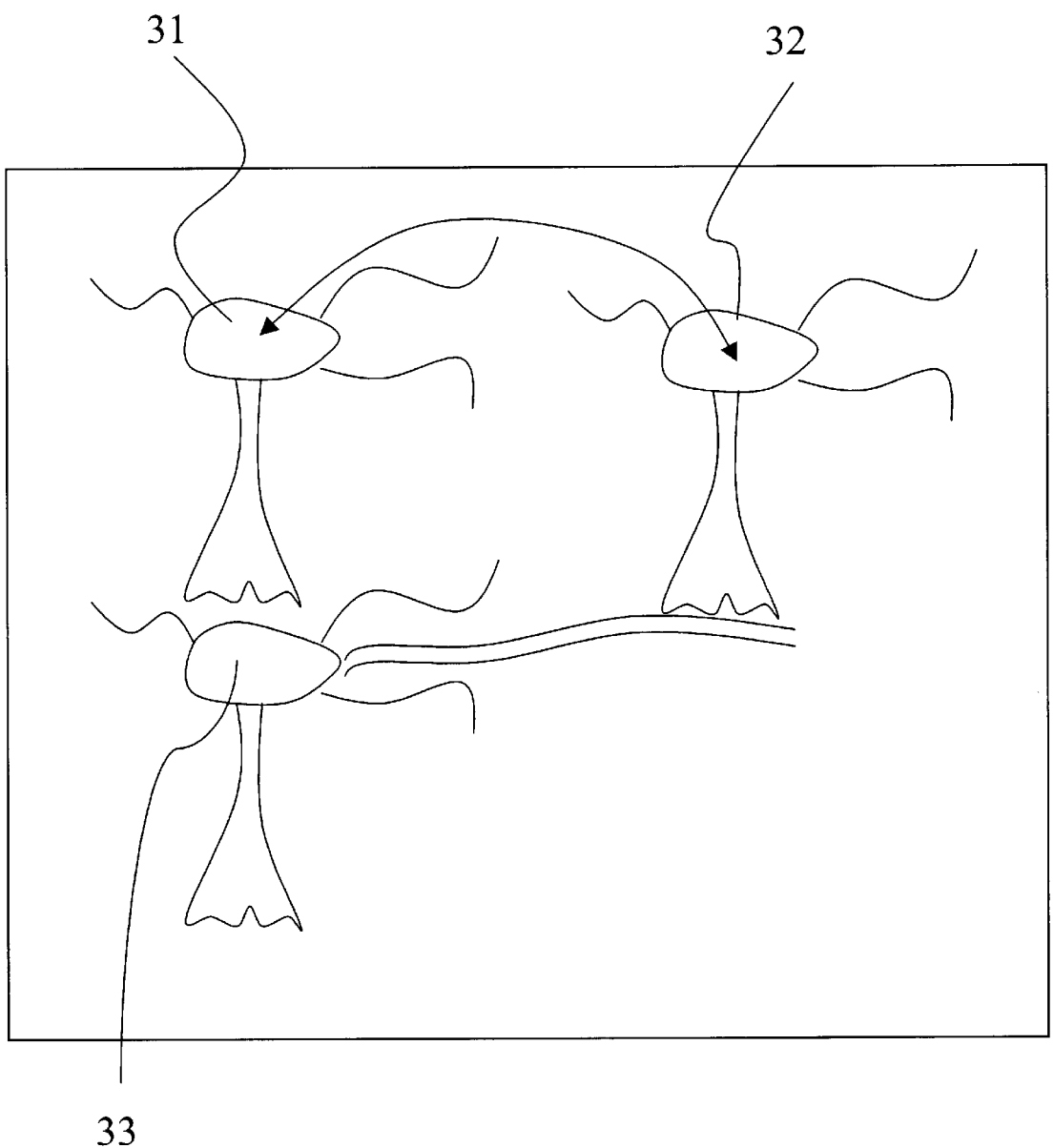
FIG. 6 schematically depicts three cells, two of which are being alternatingly and quasi-simultaneously manipulated by irradiation with UV light, while the third cell is being scanned for observation with light in the visible spectral region.

FIG. 6 shows an image with three cells 31, 32, and 33, cells 31 and 32 being alternatingly and quasi-simultaneously manipulated by irradiation with UV light. During this manipulation, third cell 33 is scanned for observation with light in the visible spectral region.

With regard to further advantageous embodiments of the method and the confocal scanning microscope according to the present invention, to avoid repetition the reader is referred to the general portion of the specification and to the appended Claims.

In conclusion, be it noted expressly that the exemplary embodiment of the confocal scanning microscope according to the present invention that is described above serves merely for discussion of the teaching claimed, but does not limit it to the exemplary embodiment.

What is claimed is:

1. A method for examining a specimen by means of a confocal scanning microscope comprising the steps of:
   generating an illuminating light beam with at least one light source,
   deflecting the illuminating light beam with to a beam deflection device over the specimen,
   acquiring a preview image;
   marking of at least one region of interest in the preview image;
   allocating individual illuminating light beam wavelengths or illuminating light beam power levels to the at least one region;
   illuminating the at least one region of the specimen in accordance with the allocation, wherein the illuminating light beam is guided such that substantially only the at least one marked region of the specimen is illuminated, and
   performing at least one manipulation in at least one region by means of the illumination wherein during the manipulation in the at least one region that region is simultaneously observed.

2. The method as defined in claim 1, wherein after illumination of the at least one region of the specimen, the reflected and fluorescent light proceeding from the specimen is detected.

3. The method as defined in claim 1, wherein during ongoing acquisition of an overview image of the at least one region, a chemical reaction is initiated or compounds are broken up by controlled, preferably time-limited introduction of the illuminating light of a second light source.

4. The method as defined in claim 3, wherein the compounds are caged calcium or caged glutamate compounds.

5. The method as defined in claim 1, wherein the manipulation comprises the excision of portions of a cell nucleus or of a complete cell nucleus.

6. The method as defined in claim 1, wherein a cell is the at least one region of interest marked in the preview image.

7. The method as defined in claim 6, wherein the cell is illuminated at a preselected point in time with UV or infrared light.

8. The method as defined in claim 1, wherein the at least one region is marked by way of a computer mouse.

9. The method as defined in claim 8, wherein the allocation of individual illuminating light beam wavelengths and illuminating light beam power levels to the at least one region is accomplished by way of a computer.

10. The method as defined in claim 1, wherein a definable blanking is performed to prevent illumination of the specimen outside the at least one region.

11. The method as defined in claim 1, wherein beam deflection between at least two regions is accomplished substantially in a direct line from one region to another region.

12. A method for examining a specimen by means of a confocal scanning microscope comprising the steps of:
   generating an illuminating light beam with at least one light source,
   deflecting the illuminating light beam with to a beam deflection device over the specimen,
   acquiring a preview image;
   marking of at least one region of interest in the preview image;
   allocating individual illuminating light beam wavelengths or illuminating light beam power levels to the at least one region;
   illuminating the at least one region of the specimen in accordance with the allocation, and
   performing at least one manipulation in at least one region by means of the illumination.

13. The method as defined in claim 12, wherein during the manipulation in the at least one region is simultaneously observed.

14. The method as defined in claim 13 wherein the manipulation comprises the excision of portions of a cell nucleus or of a complete cell nucleus.

15. The method as defined in claim 14, wherein information transmittal is detected by observation of an adjacent cell.

16. The method as defined in claim 14, wherein a reaction is initiated in two cells quasi-simultaneously or with a defined time offset.

17. The method as defined in claim 16, wherein different scan points in the two cells are alternatingly illuminated.

18. The method as defined in claim 12, wherein after illumination of the at least one region of the specimen, the reflected and fluorescent light proceeding from the specimen is detected.

19. The method as defined in claim 12, wherein during ongoing acquisition of an overview image of the at least one region, a chemical reaction is initiated or compounds are broken up by controlled, preferably time-limited introduction of the illuminating light of a second light source.

20. The method as defined in claim 19, wherein the compounds are caged calcium or caged glutamate compounds.

21. The method as defined in claim 12, wherein a definable blanking is performed to prevent illumination of the specimen outside the at least one region.

22. The method as defined in claim 12, wherein the at least one region is scanned more slowly and with elevated photon statistics as compared to the remainder of the specimen.

23. The method as defined in claim 12, wherein beam deflection between at least two regions is accomplished substantially in a direct line from one region to another region.

24. The method as defined in claim 12, wherein outside the at least one region or between the regions, the specimen is scanned at the maximum deflection speed.

25. A confocal scanning microscope comprising:

a least one light source to generate an illuminating light beam;

a beam deflection device to guide the illuminating light beam over a specimen;

a least one detector for registering the reflected and fluorescent light proceeding from the specimen;

means for acquiring a preview image of at least a part of the specimen; and means for marking at least one region of interest in the preview image, such that individual illuminating light beam and wavelengths and illuminating light beam power levels are allocated to the at least one region and thereby performing a manipulation in the at least one region.

26. The confocal scanning microscope as defined in claim 25, wherein a spectrally selective element for setting at least the illuminating light beam wavelength is provided.

27. The confocal scanning microscope as defined in claim 26, wherein the spectrally selective element is an AOTF, an AOD, an EOM, or a mechanical component and the spectrally selective element is controllable by way of a computer, preferably as a function of the deflection position.

28. The confocal scanning microscope as defined in claim 25, wherein an element for adjusting the illuminating light beam power level is provided.

29. The confocal scanning microscope as defined in claim 28, wherein the element is an AOTF or a mechanical component and the element is controllable by way of a computer, preferably as a function of the deflection position.

30. The confocal scanning microscope as defined in claim 26 or 28, wherein the element is provided for adjusting the illuminating light beam wavelength and wavelengths and for adjusting the illuminating light beam power level.

31. The confocal scanning microscope as defined in claim 25, wherein at least one laser is provided to generate the illuminating light beam.

32. The confocal scanning microscope as defined in claim 25, wherein a PC and a monitor are provided and the image or the preview image of the specimen is displayed; and the at least on the region of interest is capable of being marked via the monitor.

33. The confocal scanning microscope as defined in claim 25, wherein the beam deflection device comprises galvanometer positioning elements which are controlled by a computer, with which the beam deflection speeds are adapted individually to requirements in terms of the marked region of interest.

* * * * *